(12) United States Patent
Ni et al.

(10) Patent No.: US 7,329,226 B1
(45) Date of Patent: Feb. 12, 2008

(54) SYSTEM AND METHOD FOR ASSESSING PULMONARY PERFORMANCE THROUGH TRANSTHORACIC IMPEDANCE MONITORING

(75) Inventors: Quan Ni, Shoreview, MN (US); Jesse W. Hartley, Lino Lakes, MN (US); Kent Lee, Shoreview, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 393 days.

(21) Appl. No.: 10/885,145

(22) Filed: Jul. 6, 2004

(51) Int. Cl.
 A61N 1/39 (2006.01)
 A61N 1/00 (2006.01)
 A61B 5/08 (2006.01)
 A61B 5/05 (2006.01)

(52) U.S. Cl. .................... 600/529; 600/547; 607/2; 607/6; 607/9

(58) Field of Classification Search .............. 600/536
 See application file for complete search history.

(56) References Cited

U.S. PATENT DOCUMENTS

| 3,776,221 A | | 12/1973 | McIntyre |
| 3,832,339 A | | 8/1974 | Aisenberg et al. |
| 4,009,721 A | * | 3/1977 | Alcidi ................ 607/22 |
| 4,142,533 A | | 3/1979 | Brownlee et al. |
| 4,197,856 A | | 4/1980 | Northrop |
| 4,531,527 A | | 7/1985 | Reinhold, Jr. et al. |
| 4,548,211 A | | 10/1985 | Marks |
| 4,686,999 A | | 8/1987 | Snyder et al. |
| 4,750,495 A | * | 6/1988 | Moore et al. ............. 607/22 |
| 4,803,625 A | | 2/1989 | Fu et al. |
| 4,809,697 A | | 3/1989 | Causey, III et al. |
| 4,852,570 A | | 8/1989 | Levine |
| 4,899,758 A | | 2/1990 | Finkelstein et al. |
| 4,958,645 A | | 9/1990 | Cadell et al. |
| 4,974,607 A | | 12/1990 | Miwa |
| 4,987,897 A | | 1/1991 | Funke |

(Continued)

FOREIGN PATENT DOCUMENTS

EP 0 34 2859 11/1989

(Continued)

OTHER PUBLICATIONS

E. Braunwald, "Heart Disease - A Textbook of Cardiovascular Medicine," pp. 46-52 (5th Ed. 1997).

(Continued)

*Primary Examiner*—Charles A. Marmor, II
*Assistant Examiner*—Patricia C Mallari
(74) *Attorney, Agent, or Firm*—Patrick J. S. Inouye; Krista A. Wittman; Krystyna Szul

(57) ABSTRACT

A system and method for assessing pulmonary performance through transthoracic impedance monitoring is described. Transthoracic impedance measures are directly collected through an implantable medical device. The transthoracic impedance measures are correlated to pulmonary functional measures relative to performance of at least one respiration cycle. The transthoracic impedance measures are grouped into at least one measures set corresponding to one of an inspiratory phase and an expiratory phase. The at least one transthoracic impedance measures set are evaluated to identify a respiratory pattern relative to the inspiratory phase or the expiratory phase to represent pulmonary performance.

29 Claims, 10 Drawing Sheets

U.S. PATENT DOCUMENTS

| | | |
|---|---|---|
| 5,003,976 A | 4/1991 | Alt |
| 5,040,536 A | 8/1991 | Riff |
| 5,113,859 A | 5/1992 | Funke |
| 5,113,869 A | 5/1992 | Nappholz et al. |
| 5,133,346 A | 7/1992 | Kulkarni |
| H1114 H | 12/1992 | Schweitzer et al. |
| 5,199,428 A | 4/1993 | Obel et al. |
| 5,291,895 A | 3/1994 | McIntyre |
| 5,301,105 A | 4/1994 | Cummings, Jr. |
| 5,331,549 A | 7/1994 | Crawford, Jr. |
| 5,336,245 A | 8/1994 | Adams et al. |
| 5,355,889 A | 10/1994 | Nevo et al. |
| 5,357,427 A | 10/1994 | Langen et al. |
| 5,390,238 A | 2/1995 | Kirk et al. |
| 5,416,695 A | 5/1995 | Stutman et al. |
| 5,421,343 A | 6/1995 | Feng |
| 5,437,278 A | 8/1995 | Wilk |
| 5,438,983 A | 8/1995 | Falcone |
| 5,464,012 A | 11/1995 | Falcone |
| 5,522,860 A | 6/1996 | Molin et al. |
| 5,544,661 A | 8/1996 | Davis et al. |
| 5,553,609 A | 9/1996 | Chen et al. |
| 5,557,514 A | 9/1996 | Seare et al. |
| 5,576,952 A | 11/1996 | Stutman |
| 5,584,868 A | 12/1996 | Salo et al. |
| 5,591,215 A | 1/1997 | Greenhut et al. |
| 5,603,331 A | 2/1997 | Heemels et al. |
| 5,660,183 A | 8/1997 | Chiang et al. |
| 5,673,691 A | 10/1997 | Abrams et al. |
| 5,687,734 A | 11/1997 | Dempsey et al. |
| 5,697,959 A | 12/1997 | Poore |
| 5,704,345 A | 1/1998 | Berthon-Jones |
| 5,704,366 A | 1/1998 | Tracklind et al. |
| 5,711,297 A | 1/1998 | Iliff |
| 5,713,350 A | 2/1998 | Yokota et al. |
| 5,720,770 A | 2/1998 | Nappholz et al. |
| 5,720,771 A | 2/1998 | Snell |
| 5,724,580 A | 3/1998 | Levin et al. |
| 5,724,983 A | 3/1998 | Selker et al. |
| 5,738,102 A | 4/1998 | Lemelson |
| 5,743,267 A | 4/1998 | Nikolic |
| 5,749,907 A | 5/1998 | Mann |
| 5,749,908 A | 5/1998 | Snell |
| 5,752,976 A | 5/1998 | Duffin et al. |
| 5,769,074 A | 6/1998 | Barnhill et al. |
| 5,772,586 A | 6/1998 | Heinonen et al. |
| 5,772,599 A | 6/1998 | Nevo et al. |
| 5,772,604 A | 6/1998 | Langberg et al. |
| 5,778,882 A | 7/1998 | Raymond et al. |
| 5,785,650 A | 7/1998 | Akasaka et al. |
| 5,785,660 A | 7/1998 | Van Lake et al. |
| 5,788,640 A | 8/1998 | Peters |
| 5,788,643 A | 8/1998 | Feldman |
| 5,792,062 A | 8/1998 | Poon et al. |
| 5,819,251 A | 10/1998 | Kremer et al. |
| 5,855,593 A | 1/1999 | Olson et al. |
| 5,860,918 A | 1/1999 | Schradi et al. |
| 5,876,353 A | 3/1999 | Riff |
| 5,879,375 A | 3/1999 | Larson, Jr. et al. |
| 5,891,178 A | 4/1999 | Mann et al. |
| 5,897,493 A | 4/1999 | Brown |
| 5,911,132 A | 6/1999 | Sloane |
| 5,931,857 A | 8/1999 | Prieve et al. |
| 5,954,640 A | 9/1999 | Szabo |
| 5,957,861 A | 9/1999 | Combs et al. |
| 5,974,124 A | 10/1999 | Schlueter, Jr. et al. |
| 5,987,352 A | 11/1999 | Klein et al. |
| 5,993,386 A | 11/1999 | Ericsson |
| 6,004,276 A | 12/1999 | Wright et al. |
| 6,014,581 A | 1/2000 | Whayne et al. |
| 6,024,699 A | 2/2000 | Surwit et al. |
| 6,038,469 A | 3/2000 | Karlsson et al. |
| 6,047,203 A | 4/2000 | Sackner et al. |
| 6,050,940 A | 4/2000 | Braun |
| 6,063,028 A | 5/2000 | Luciano |
| 6,067,466 A | 5/2000 | Selker |
| 6,073,046 A | 6/2000 | Patel |
| 6,080,106 A | 6/2000 | Lloyd et al. |
| 6,083,248 A | 7/2000 | Thompson |
| 6,093,146 A | 7/2000 | Filangeri |
| 6,095,985 A | 8/2000 | Raymond et al. |
| 6,102,856 A | 8/2000 | Groff et al. |
| 6,120,442 A | 9/2000 | Hickey |
| 6,122,351 A | 9/2000 | Schlueter, Jr. et al. |
| 6,129,675 A | 10/2000 | Jay |
| 6,132,384 A | 10/2000 | Christopherson et al. |
| 6,135,951 A | 10/2000 | Richardson et al. |
| 6,139,494 A | 10/2000 | Cairnes |
| 6,152,882 A | 11/2000 | Prutchi |
| 6,155,267 A | 12/2000 | Nelson |
| 6,168,563 B1 | 1/2001 | Brown |
| 6,168,653 B1 | 1/2001 | Myers |
| 6,171,237 B1 | 1/2001 | Avitall et al. |
| 6,171,256 B1 | 1/2001 | Joo et al. |
| 6,223,078 B1 | 4/2001 | Marcovecchio |
| 6,225,901 B1 | 5/2001 | Kail, IV |
| 6,234,964 B1 | 5/2001 | Iliff |
| 6,238,349 B1 | 5/2001 | Hickey |
| 6,246,992 B1 | 6/2001 | Brown |
| 6,249,705 B1 | 6/2001 | Snell |
| 6,250,309 B1 | 6/2001 | Krichen et al. |
| 6,263,245 B1 | 7/2001 | Snell |
| 6,283,923 B1 | 9/2001 | Finkelstein et al. |
| 6,287,252 B1 | 9/2001 | Lugo |
| 6,290,646 B1 | 9/2001 | Cosentino et al. |
| 6,302,844 B1 | 10/2001 | Walker et al. |
| 6,306,088 B1 | 10/2001 | Krausman et al. |
| 6,336,900 B1 | 1/2002 | Alleckson |
| 6,363,282 B1 | 3/2002 | Nichols et al. |
| 6,416,471 B1 | 7/2002 | Kumar |
| 6,428,483 B1 | 8/2002 | Carlebach |
| 6,442,433 B1 | 8/2002 | Linberg |
| 6,454,705 B1 | 9/2002 | Cosentino et al. |
| 6,463,326 B1 | 10/2002 | Hartley et al. |
| 6,477,424 B1 | 11/2002 | Thompson et al. |
| 6,512,949 B1 | 1/2003 | Combs et al. |
| 6,662,032 B1 | 12/2003 | Gavish et al. |
| 6,795,733 B1 * | 9/2004 | Lu .............................. 607/17 |
| 6,827,670 B1 | 12/2004 | Stark et al. |
| 2002/0123674 A1 | 9/2002 | Plicchi et al. |
| 2003/0055679 A1 | 3/2003 | Soll et al. |
| 2003/0153954 A1 * | 8/2003 | Park et al. .................... 607/17 |
| 2004/0111040 A1 * | 6/2004 | Ni et al. ...................... 600/534 |
| 2005/0065567 A1 * | 3/2005 | Lee et al. ..................... 607/17 |

FOREIGN PATENT DOCUMENTS

| | | |
|---|---|---|
| EP | 0 513 457 | 11/1992 |
| EP | 0 531 889 | 3/1993 |
| EP | 0 711 531 | 5/1996 |
| WO | WO 97/39792 | 10/1997 |
| WO | WO 98/01742 | 2/1998 |
| WO | WO 98/42103 | 9/1998 |
| WO | WO 99/46718 | 9/1999 |
| WO | WO 99/55226 | 11/1999 |

OTHER PUBLICATIONS

Hamilton et al., "Arterial, Cerebrospinal and Venous Pressures in Man During Cough and Strain, "144 Am. J. of Phys., pp. 42, 42-50 (1944).

Zema et al., "Left Ventricular Dysfunction - Bedside Valsalva Maneuver, "Br. Heart J., pp. 44:560-569 (1980).

McKay et al., "Instantaneous Measurement of Left and Right Venticular Stroke Volume and Pressure-Volume Relationships with an Impedance Catheter, "Circ. 69, No. 4, pp. 703-710 (1984).

Wortel et al., "Impedance Measurements in the Human Right Ventricle Using a New Pacing System, "Pacing Clinical Electrophysiology, vol. 14(9), pp. 1336-42 (Sep. 1991).

Seborg et al., "Process Dynamics and Control, "pp. 165-167, John Wiley & Sons (1989).

Dunn et al., "Telemedicine Links Patients in Sioux Lookout with Doctors in Toronto, "CMA Journal, vol. 122, pp. 484-487 (Feb. 23, 1980).

Auer et al., "Paced Epimyocardial Electrograms for Noninvasive Rejection Monitoring After Heart Transplantation, "The Journal of Heart and Lung Transplantation, vol. 15, No. 10, pp. 993-998 (Oct. 1996).

Schreier et al., "A Non-Invasive Rejection Monitoring System Based on Remote Analysis of Intramyocardial Electrograms from Heart Transplants, "IEEE, pp. 35-36 (1997).

Roberge et al., "Basic and Applied Biomedical Engineering Building Blocks for Health Care, "1995 IEEE Engineering in Medicine and Biology 17th Annual Conference, vol. 1, Montreal-Canada, (Sep. 20-23, 1995).

Hutten et al., "Cardiac Telemonitoring by Intergrating Pacemaker Telemetry within Worldwide Data Communication Systems, "Proceedings of 19th International Conference, IEEE/EMBS, Chicago, IL, pp. 974-976 (Oct. 30- Nov. 2, 1997).

Vargas, Juan E., "Home-Based Monitoring of Cardiac Patients, "Dept. of Electr. & Comput. Eng., South Carolina Univ., Columbia, SC, Information Technology Applications in Biomedicine, Proceedings., 1998 IEEE International Conference, pp. 133-136 (May 16-17, 1998).

Magrabi et al., "Web Based Longitudinal ECG Monitoring, "Proceedings of 20th Annual International Conference of the IEEE Engineering in Medicine and Biology Society, vol. 20, No. 3, pp. 1115-1158 (1998).

Nelwan et al., "Ubiquitous Acccess to Real-Time Patient Monitoring Data, "Computers in Cardiollogy., vol. 24, pp. 271-274 (1997).

Moody GB, "Integration of Real-Time and Off-Line Clinical Data in the MIMIC Database, "Computers in Cardiology 1997 vol. 24, pp. 585-588, Cambridge, MA USA.

Long WJ, et al., "Differential Diagnosis Generation from a Casual Network with Probabilities, "Computers in Cardiology, 1988, Proceedings, pp. 185-188, Washington DC, USA.

* cited by examiner

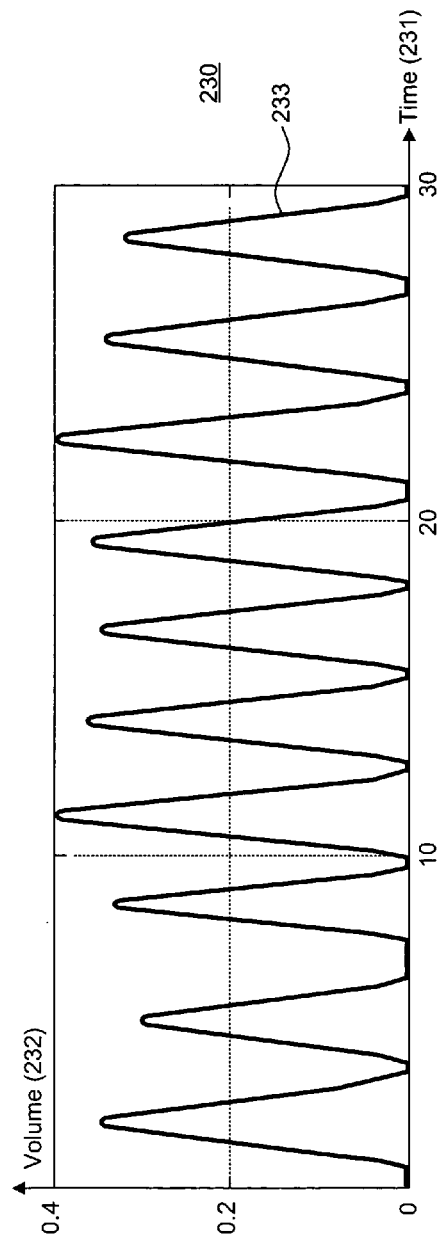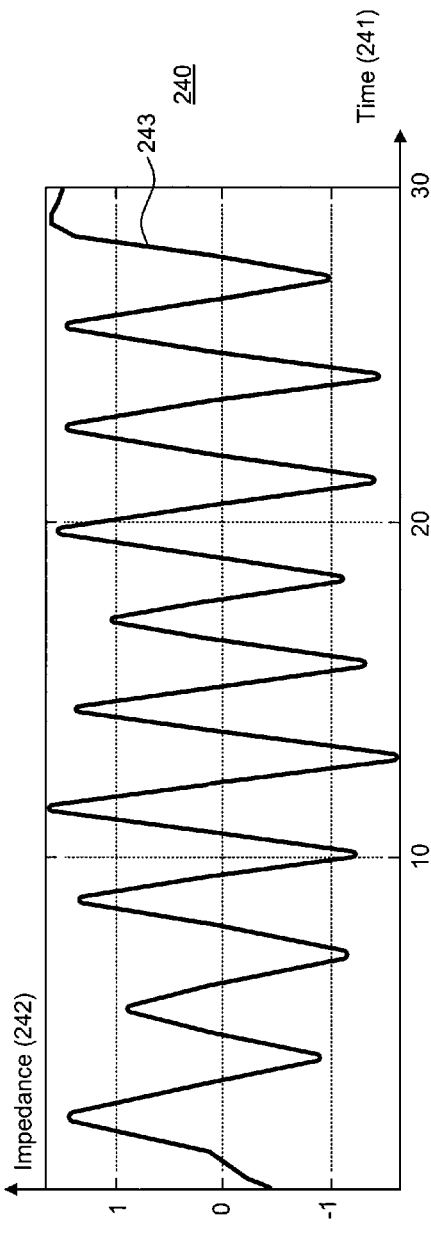

270

SYSTEM AND METHOD FOR ASSESSING PULMONARY PERFORMANCE THROUGH TRANSTHORACIC IMPEDANCE MONITORING

FIELD OF THE INVENTION

The present invention relates in general to pulmonary performance assessment and, in particular, to a system and method for assessing pulmonary performance through transthoracic impedance monitoring.

BACKGROUND OF THE INVENTION

Pulmonary diseases and disorders continue to pose major health care concerns. According to the American Lung Association, pulmonary diseases and other breathing problems were the third leading cause of death in the United States in 2003, responsible for one in seven deaths, with more than 35 million Americans suffering from chronic pulmonary diseases.

Pulmonary diseases and disorders are of either an obstructive or restrictive nature. Obstructive breathing diseases are caused by a blockage or obstacle is the airway due to injury or disease, such as asthma, chronic bronchitis, emphysema, or advanced bronchiectasis. Restrictive breathing disorders are caused by muscular weakness, a loss of lung tissue or when lung expansion is limited as a result of decreased compliance of the lung or thorax. The conditions that can result in a restrictive breathing disorder include pectus excavatum, myasthenia gravis, diffuse idiopathic interstitial fibrosis, and space occupying lesions, such as tumors and effusions. Proper treatment of pulmonary diseases and disorders requires early identification and on-going monitoring of pulmonary performance.

Conventionally, pulmonary performance is tested in a clinical setting to establish certain baseline values indicative of the ability of the lungs to exchange oxygen and carbon dioxide during normal breathing. Pulmonary performance can be established by testing pulmonary volumes using a spirometer during inspiration and expiration, as measured under normal and forced conditions. Spirometric testing can determine tidal volume ($V_T$), which is the volume inhaled or exhaled in normal quiet breathing; inspiratory reserve volume (IRV), which is the maximum volume that can be inhaled following a normal quiet inhalation; expiratory reserve volume (ERV), which is the maximum volume that can be exhaled following a normal quiet exhalation; and inspiratory capacity (IC), which is the maximum volume that can be inhaled following a normal quiet exhalation.

In addition, functional residual capacity (FRC), which is the volume remaining in the lungs following a normal quiet exhalation, can be measured by introducing helium into a closed spirometer at the end of a normal quiet exhalation and determining FRC from helium concentration upon reaching equilibrium. However, for patients suffering from obstructive respiratory disorders, such as emphysema, the helium dilution technique can underestimate FRC. Alternatively, FRC can also be measured through body plethysmography.

Pulmonary performance testing in a non-clinical setting is difficult. Testing requires the same equipment as required in-clinic. Moreover, ensuring that the battery of pulmonary performance tests, in particular, forced expiration, is accurately and consistently administered can be difficult for lay people. Consequently, ambulatory pulmonary performance testing results generally lack a sufficient degree of reliability for use in medical diagnosis and treatment. Implantable medical devices facilitate ambulatory in situ physiological testing and monitoring, but conventional applications of implantable medical device measurement failed to provide an adequate solution to ambulatory pulmonary performance testing.

U.S. Patent Application Publication No. US2002/0123674, filed Feb. 27, 2002, by Plicchi et al., describes an implantable medical device capable of detecting the physiological properties of pulmonary tissue, which are dependent on the density and variations caused by the pathologic condition of the heart. Intrapulmonary catheters with sensors are inserted into pulmonary arteries. The sensors allow ambulatory monitoring of electrocardiographic (ECG) signals without the artifacts or interferences, such as myoelectric artifacts and muscular tremors, occasioned by the use of external ECG sensors. However, the placement of intrapulmonary catheters is highly invasive and the approach relies upon the bioelectric impedance of the pulmonary tissues to precisely measure R-waves and related physiological signals. Moreover, the Plicchi device is focused on determining lung density and fluid volume and not on measuring transthoracic impedance to determine pulmonary volume and rates.

U.S. Pat. No. 5,957,861, issued Sep. 28, 1999 to Combs et al., describes an implantable edema monitor with a pair of electrically isolated electrodes implanted in subcutaneous regions of the body. Energy pulses are delivered from the housing of the monitor to the electrodes to determine pulmonary impedance. The monitor can be used with pacemakers or other implantable cardiac devices. The monitor stores short term and long term average impedance values and identifies diagnostically significant events. However, the Combs monitor focuses on sensing impedance as an indication of edema and not on deriving volumetric or rate values relating to cardiopulmonary functioning.

U.S. Pat. No. 5,522,860, issued Jun. 4, 1996 to Molin et al., describes an implantable medical device that counts noise events occurring due to parasitic electromagnetic signals. In one embodiment, if the noise values are too high or there is too much noise at unacceptable levels, an acquired pulmonary impedance value may be discarded as being unreliable. The Molin device focuses on sensed physiological values, not volumetric and rate-related cardiopulmonary values, and whether to suspend operation due to noise levels exceeding predefined thresholds.

U.S. Pat. No. 5,003,976, issued Apr. 2, 1991 to Alt, describes an apparatus for deriving the physiological activities of a patient through detection and analysis with a single sensor implanted in the vascular system of the patient. The pulmonary activities are derived from differences in cardiac activities, including blood flow, pressure and volume changes, and performance measures observed through right heart impedance changes. The Alt device relies on a single functional parameter, intracardiac impedance, that is representative of both cardiac and pulmonary activity and as distinguished through the use of high pass low pass filters. However, the Alt device only measures impedance with respect to pulmonary activities derived from measures collected through the vascular system and not through transthoracic sensors representative of volumetric or rate-related cardiopulmonary values.

Therefore, there is a need for an approach to assessing pulmonary performance by measuring volumetric and rate profile data through transthoracic impedance, particularly as related to the performance of a forced expiration maneuver. Preferably, such an approach would facilitate analyzing pulmonary performance in a non-clinical setting on a regular basis for use in automated pulmonary and cardiopulmonary disease patient measurement.

SUMMARY OF THE INVENTION

A system and method for providing an ambulatory-based pulmonary performance evaluation is described. Transthoracic impedance measures are collected during the performance of respiration cycles, which preferably includes a forced expiration, using an implantable medical device. The start of a forced expiration is either expressly marked by the patient or implicitly derived by the implantable medical device or by a transthoracic pressure sensing device. The collected transthoracic impedance measures are periodically evaluated for determining a pulmonary volume profile. The transthoracic impedance measures are correlated to cardiopulmonary volumetric and rate measures and are assigned to the respective inspiratory and expiratory phases of each respiration cycle. A pulmonary volume profile is determined and an overall set of trends is identified by comparison to previously-observed pulmonary volume profiles. The trends are interpreted against predicted values to provide a morphological indication of the presence of an obstructive or restrictive respiratory pattern.

An embodiment provides a system and method for assessing pulmonary performance through transthoracic impedance monitoring. Transthoracic impedance measures are directly collected through an implantable medical device. The transthoracic impedance measures are correlated to pulmonary functional measures relative to performance of at least one respiration cycle. The transthoracic impedance measures are grouped into at least one measures set corresponding to one of an inspiratory phase and an expiratory phase. The at least one transthoracic impedance measures set are evaluated to identify a respiratory pattern relative to the inspiratory phase or the expiratory phase to represent pulmonary performance.

Still other embodiments of the present invention will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIGS. 7A-B are graphical representations showing, by way of example, trend analysis for a volume profile during a forced expiration.

DETAILED DESCRIPTION

Transthoracic Impedance Monitoring Using Implantable Medical Device

Figure 1:
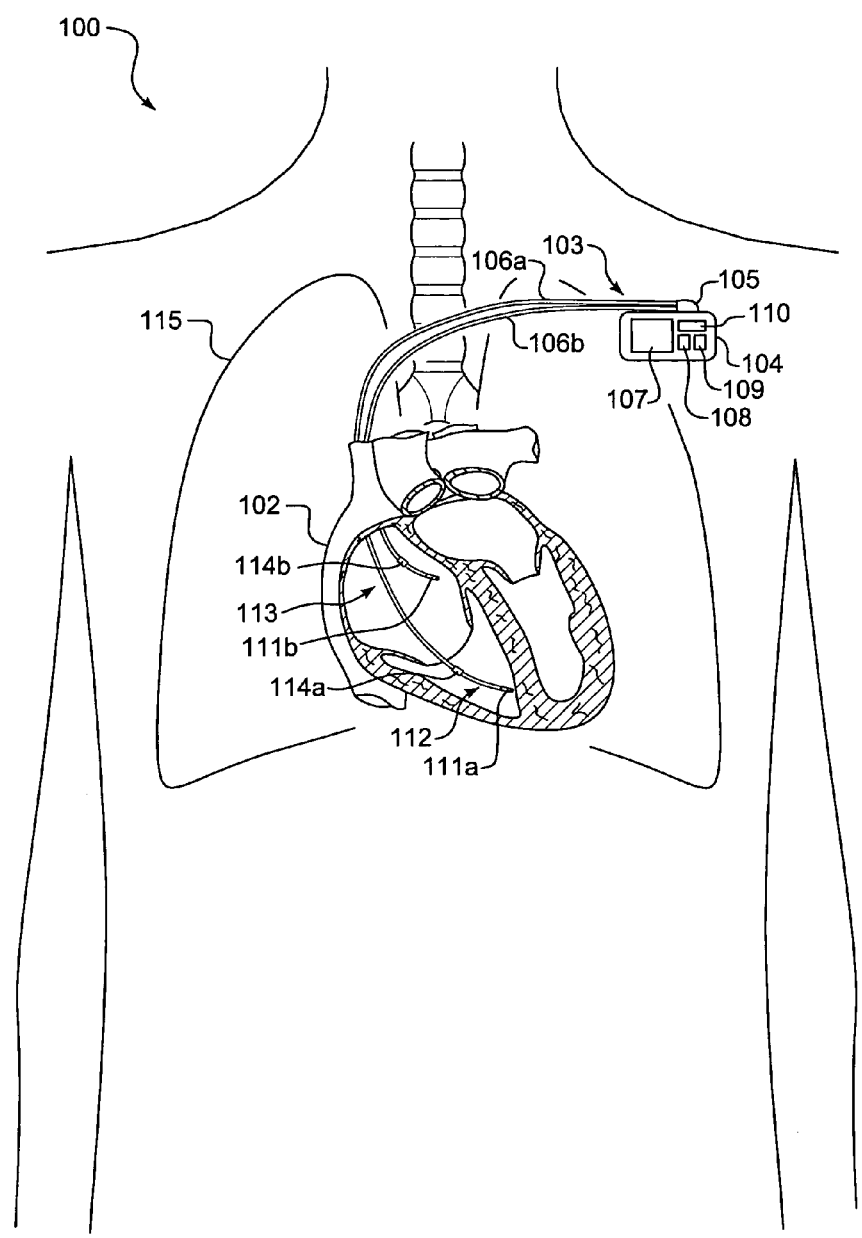
FIG. 1 is a schematic diagram showing an implantable medical device for monitoring transthoracic impedance.

FIG. 1 is a schematic diagram 100 showing an implantable medical device (IMD) 103 monitoring transthoracic impedance, in accordance with a further embodiment of the present invention. The IMD 103 is surgically implanted in the chest or abdomen of a patient and consists generally of a housing 104 and terminal block 105. The IMD 103 is coupled to a set of leads 106a-b at the terminal block 105. During surgery, the leads 106a-b are threaded through a vein and placed into the heart 102 with the distal tips of each lead 106a-b positioned in direct contact with tissue inside the heart 102.

The housing 104 contains a battery 107, control circuitry 108, memory 109, and telemetry circuitry 110. The battery 107 provides a finite power source for the IMD components. The control circuitry 108 samples and processes raw data signals and includes signal filters and amplifiers, memory and a microprocessor-based controller, as would be appreciated by one skilled in the art. The memory 109 includes a short-term, volatile memory store in which raw physiological signals can be stored as telemetered signals for later retrieval and analysis. The telemetry circuitry 110 provides an interface between the IMD 103 and external devices (not shown). The telemetry circuitry 110 enables operating parameters to be non-invasively programmed into the memory 109 through an external device in telemetric communication with the IMD 103. The telemetry circuitry 110 also allows patient information collected by the IMD 103 and transiently stored in the memory 109 to be sent to the external device for processing and analysis.

The IMD 103 is in direct electrical communication with the heart 102 through electrodes 111a-b positioned on the distal tips of each lead 106a-b. By way of example, the set of leads 106a-b can include a right ventricular electrode 111a and a right atrial electrode 111b. The right ventricular electrode 111a is preferably placed in the right ventricular apex 112 of the heart 102 and the right atrial electrode 111b is preferably placed in the tight atrial chamber 113 of the heart 102. The electrodes 111a-b enable the IMD 103 to directly collect raw physiological measures, preferably through millivolt measurements. The set of leads 106a-b can also include a right ventricular electrode 114a and a right atrial electrode 114b respectively located proximal to the right ventricular electrode 111a and the right atrial electrode 111b. The electrodes 114a-b enable the IM 103 to inject a sub-threshold stimulating current between the housing 104 and the electrodes 114a-b. The voltage across the housing 104 and at either or both of the electrodes 111a-b can be measured to determine transthoracic impedance, from which respiratory rate, tidal volume and minute ventilation can be determined. In a further embodiment, oxygen saturation can also be measured by including an oxygen saturation sensor within one or both of the electrodes 114a-b for use in evaluating blood gases. In a still further embodiment, the electrodes 114a-b can include and be configured as a reference electrode and sensor for determining pH information. Other configurations and arrangements of leads, electrodes and sensors, including the use of single and multiple leads arrays and single and multiple electrodes sensors, can be used, as would be recognized by one skilled in the art.

In the described embodiment, the IMD 103 can be implemented as part of cardiac pacemakers used for managing bradycardia, implantable cardioverter defibrillators (IMDs) used for treating tachycardia, and other types of implantable cardiovascular monitors and therapeutic devices used for monitoring and treating heart failure, structural problems of the heart, such as congestive heart failure, rhythm problems, and other heart conditions, as would be appreciated by one skilled in the art. Examples of cardiac pacemakers suitable for use in the described embodiment include the Pulsar Max II pacing systems, sold by Guidant Corporation, St. Paul, Minn. Further examples of cardiac pacemakers that sense transthoracic impedance are described generally in "The Exercise Responsive Cardiac Pacemaker," IEEE Trans. on Biomedical Eng'g, Vol. 12 (December 1984), and in U.S. Pat. No. 4,750,495, issued Jun. 14, 1998 to Moore et al. and U.S. Pat. No. 6,463,326, issued Oct. 8, 2002 to Hartley et al., the disclosures of which are incorporated by reference. A related fiber-optic oxygen saturation and hematocrit sensor is described in U.S. Statutory Invention Registration No. H1,114, published Dec. 1, 1992, the disclosure of which is incorporated by reference.

On a regular basis, the telemetered signals, including collected respiratory rate, tidal volume and minute ventilation values and, in a further embodiment, oxygen saturation and pH data, stored in the memory 109 are retrieved. By way of example, a programmer (not shown) can be used to retrieve the telemetered signals. However, any form of programmer, interrogator, recorder, monitor, or telemetered signals transceiver suitable for communicating with IMD 103 could be used, as would be appreciated by one skilled in the art. In addition, a server, personal computer or digital data processor could be interfaced to the IMD 103, either directly or via a telemetered signals transceiver configured to communicate with the implantable medical device 103.

The programmer communicates with the IMD 103 via radio frequency signals exchanged through a wand placed over the location of the IMD 103. Programming or interrogating instructions are sent to the IMD 103 and the stored telemetered signals are downloaded into the programmer. Once downloaded, the telemetered signals can be sent via a network, such as the Internet, to a server (not shown), which periodically receives, stores and processes the telemetered signals in a database, as further described below with reference to FIG. 3.

An example of a programmer suitable for use in the present invention is the Model 2901 Programmer Recorder Monitor, manufactured by Guidant Corporation, Indianapolis, Ind., which includes the capability to store retrieved telemetered signals on a proprietary removable floppy diskette. The telemetered signals could later be electronically transferred using a personal computer or similar processing device, as would be appreciated by one skilled in the art.

Other alternate telemetered signals transfer means could also be employed. For instance, the stored telemetered signals could be retrieved from the IMD 103 and electronically transferred to a network using a combination of a remote external programmer and analyzer and a remote telephonic communicator, such as described in U.S. Pat. No. 5,113,869, the disclosure of which is incorporated by reference. Similarly, the stored telemetered signals could be retrieved and remotely downloaded to a server using a world-wide patient location and data telemetry system, such as described in U.S. Pat. No. 5,752,976, the disclosure of which is incorporated herein by reference.

Process Flow

Figure 2:
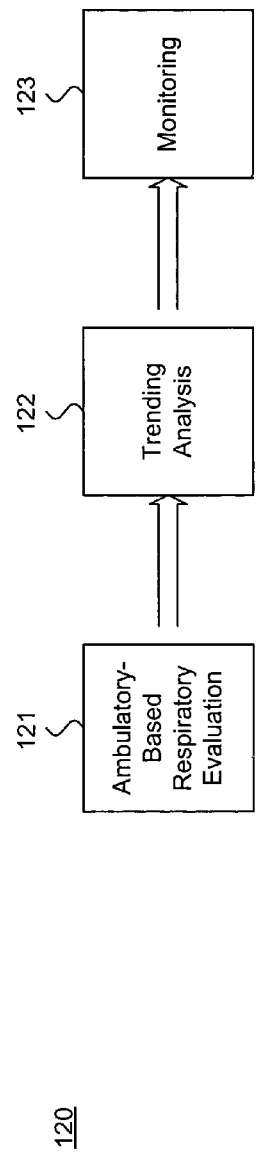
FIG. 2 is a process flow diagram showing the operations performed to assess pulmonary performance.

FIG. 2 is a process flow diagram 120 showing the operations performed to assess pulmonary performance. The process is performed on an ambulatory patient-specific basis. Initially, an ambulatory-based respiratory evaluation is performed (operation 121) by the patient through monitoring provided by the IMD 103. The IMD 103 measures the variations in transthoracic impedance, which increases during the inspiratory and decreases during the expiratory phases of respiration cycles. Respiratory rate, tidal volume and minute ventilation can be directly measured. In addition, when the impedance sensor using one or more electrodes 114a-b and 111a-b are calibrated, the IMD 103 can also be used to measure forced vital capacity (FVC) and force expiratory volume (FEV) during forced expiration. The measurements are regularly collected and stored by the IMD 103 and are periodically retrieved for processing during the second phase of pulmonary performance assessment.

The physiological measures recorded by the IMD 103 are retrieved from the IMD 103 and either the programmer or the server performs a trending analysis (operation 122) and monitoring (operation 123) of the patient. In a further embodiment, the trending analysis and monitoring are performed by the IMD 103, which does not need to retrieve the physiological measures. The trending analysis (operation 122) includes deriving the ratio of FEV to FVC, rates of change, and forced expiratory flow components to differentiate between obstructive and restrictive respiratory pattern, as further described below with reference to FIGS. 7A-C. In a further embodiment, a sensor baseline is established and relative changes to FEV and FVC are determined to facilitate identifying a morphology indicative of a restrictive respiratory pattern. In a still further embodiment, the ratio of FEV to FVC, forced expiratory flow and maximal midexpiratory flow rate (MMFR) are determined without requiring sensor calibration to facilitate identifying a morphology indicative of an obstructive respiratory pattern.

During monitoring (operation 123), the pulmonary performance of the patient is followed through an automated patient measurement care system, as further described below with reference to FIG. 4. Briefly, the patient care system performs the trending analyses (operation 124) and integrates the physiological measures obtained through ambulatory-based respiratory evaluation (operation 121) with further physiological measures obtained in-clinic. For example, the functional residual capacity and residual volume, which is the volume remaining in the lungs following a maximal exhalation, can be measured in-clinic through the use of a body plethysmography. Various related measures can be further derived and analyzed against predefined thresholds to generate alerts to healthcare providers upon a sufficient deviation.

Pulmonary Performance Assessment System

Figure 3:
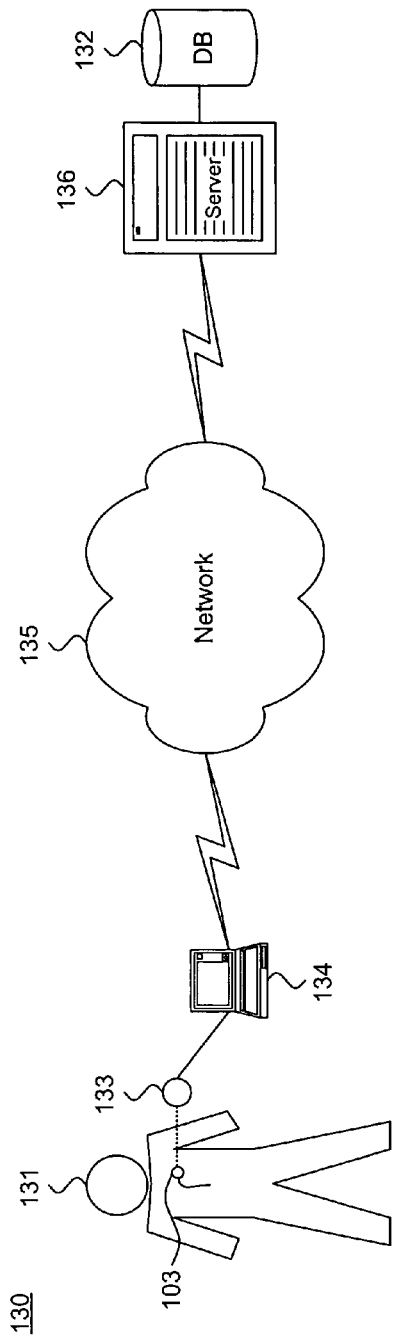
FIG. 3 is a block diagram showing a system for assessing pulmonary performance through transthoracic impedance monitoring, in accordance with an embodiment of the invention.

FIG. 3 is a block diagram showing a system 130 for assessing pulmonary performance through transthoracic impedance monitoring, in accordance with an embodiment of the invention. A patient 131 is a recipient of an IMD 103, such as, by way of example, an implantable pulse generator or heart failure or event monitor, with a set of leads extending into his or her heart. The IMD 103 includes circuitry for recording into a short-term, volatile memory telemetered signals, which are stored as a set of collected measures for later retrieval. For an exemplary IMD 103, the telemetered signals non-exclusively present patient information recorded on a per heart beat, binned average or derived basis and relating to respiratory rate, tidal volume and minute ventilation and, in a further embodiment, oxygen saturation and pH levels, as further described above with reference to FIG. 1.

The telemetered signals stored in the IMD 103 are retrieved upon the completion of an initial observation baseline period and subsequently retrieved on a preferably continuous, periodic monitoring basis to monitor transthoracic impedance. The initial observation period establishes a reference baseline pulmonary performance assessment and the subsequent data sets enable a healthcare provider to follow the physical well-being of the patient 131 through ambulatory-based respiratory evaluations. In particular, during the initial observation period and subsequent evaluations, the patient 131 performs a pattern of forced expirations, during which FVC and FEV are measured and related rate and volumetric components can be derived.

By way of example, a programmer 134 can be used to retrieve the telemetered signals. However, any form of programmer, interrogator, recorder, monitor, or telemetered signals transceiver suitable for communicating with IMD 103 could be used, as would be appreciated by one skilled in the art. In addition, a server, personal computer or digital data processor could be interfaced to the IMD 103, either directly or via a telemetered signals transceiver configured to communicate with the implantable medical device 103.

The programmer 134 communicates with the IMD 103 via radio frequency signals exchanged through a wand 133 placed over the location of the IMD 103. Programming or interrogating instructions are sent to the IMD 103 and the stored telemetered signals are downloaded into the programmer 134. Once downloaded, the telemetered signals can be sent via a network 135, such as the Internet, to a server 136, which periodically receives and stores the telemetered signals in a database 132, as further described below with reference to FIG. 4.

An example of a programmer suitable for use in the present invention is the Model 2901 Programmer Recorder Monitor, manufactured by Guidant Corporation, Indianapolis, Ind., which includes the capability to store retrieved telemetered signals on a proprietary removable floppy diskette. The telemetered signals could later be electronically transferred using a personal computer or similar processing device, as would be appreciated by one skilled in the art.

Other alternate telemetered signals transfer means could also be employed. For instance, the stored telemetered signals could be retrieved from the IMD 103 and electronically transferred to a network using a combination of a remote external programmer and analyzer and a remote telephonic communicator, such as described in U.S. Pat. No. 5,113,869, the disclosure of which is incorporated by reference. Similarly, the stored telemetered signals could be retrieved and remotely downloaded to a server using a world-wide patient location and data telemetry system, such as described in U.S. Pat. No. 5,752,976, the disclosure of which is incorporated herein by reference.

The server 136 includes a general purpose, programmed digital computing device, including a central processing unit, random access memory, non-volatile secondary storage, such as a hard drive or CD ROM drive, network or wireless interfaces, and peripheral devices, including user interfacing means, such as a keyboard and display. Program code, including software programs, and data is loaded into the RAM for execution and processing by the CPU and results are generated for display, output, transmittal, or storage.

Server Analyzing Pulmonary Functional Measures

Figure 4:
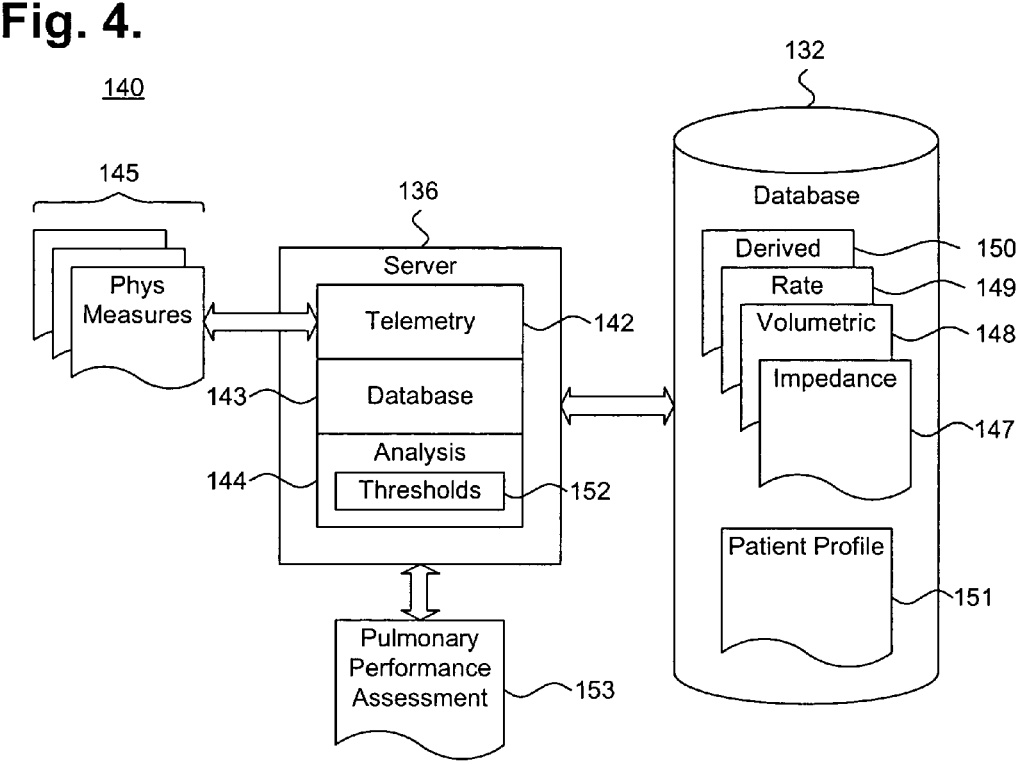
FIG. 4 is a functional block diagram showing a server for use in the system of FIG. 2.

FIG. 4 is a functional block diagram 140 showing a server 136 for use in the system of FIG. 2. Each component is a computer program, procedure or process written as source code in a conventional programming language, such as the C++ programming language, and is presented for execution by one or more CPUs as object or byte code in a uniprocessing, distributed or parallelized configuration, as would be appreciated by one skilled in the art. The various implementations of the source code and object and byte codes can be held on a computer-readable storage medium or embodied on a transmission medium in a carrier wave.

The system 140 consists of a server 136 coupled to a database 132, which provides persistent secondary storage. The server 136 includes telemetry 142, database 143, and analysis 144 modules. The telemetry module 142 is communicatively interfaced over the network 135 to the programmer 134. The telemetry module 142 receives physiological measures 145 from the programmer 134 following retrieval of the physiological measures 145 from the IMD 103. The physiological measures 145 include raw physiological data regularly collected by the IMD 103 during initial and subsequent pulmonary performance assessments and stored in the memory 109 of the IMD 103. The telemetry module 142 communicates with the telemetry circuitry 110 on the IMD 103 using standard programmer communication protocols, as would be appreciated by one skilled in the art.

In a further embodiment, the telemetry module 142 directly communicatively interfaces to the IMD 103 through a logically-formed, non-invasive communication channel, such as provided though induction, static magnetic field coupling, or by related means, as would be appreciated by one skilled in the art. The telemetry module 142 facilitates the transferal and exchange of physiological measures 145 between the IMD 103 and the server 136.

The database module 143 maintains information stored in the database 132 as structured records for facilitating efficient storage and retrieval. The database module 143 stores the physiological measures 145 received from the IMD 103 in the database 132. The database 132 stores the physiological measures 145 as derived measures, which include, non-exclusively, impedance measures 147, pulmonary volumetric measures 148, pulmonary rate measures 149, and derived measures 150. Other raw and derived measures can be stored in the database 132, as would be recognized by one skilled in the art. In addition, patient profile information 151 can be maintained in the database 132.

The analysis module 144 derives and evaluates the physiological data maintained in the database 132. As necessary, the physiological measures 145 retrieved from the IMD 103 are converted and derived into the impedance measures 147, pulmonary volumetric measures 148, pulmonary rate measures 149, and derived measures 150, as would be appreciated by one skilled in the art. In particular, the impedance measures 147 are analyzed and evaluated to determine an overall pulmonary volume profile. The profile can be compared to predefined thresholds 152 for assessing pulmonary performance, particularly relative to the performance of forced expiration, as further described below with reference to FIG. 11. The analysis module 144 generates a pulmonary performance assessment 153, which identifies trends indicating an absence, onset, progression, regression, and status quo of pulmonary and cardiopulmonary diseases. The pulmonary performance assessment 153 can be further evaluated to determine whether medical intervention is necessary.

The pulmonary performance assessment 153 reflects the actual observed pulmonary physiology for a given person, which varies with the age and size of the patient. Normal expected pulmonary performance values are calculated using prediction equations or nomograms, which provide normal values for a specific age, height and sex. The observed values are generally reported as a percentage of the predicted value. The prediction equations are derived using linear regression on data from a population of normal subjects, such as described below in Table 1, which provides an example of reference values for commonly used pulmonary function testing for white, non-smoking adults in the U.S. J. E. Cotes, "Lung Function," $5^{th}$ ed. Oxford: Blackwell (1993). In Table 1, Ht refers to height (in meters), A refers to age (in years) and standard deviation is indicated in parentheses. Other predictive metrics could also be used.

TABLE 1

|  | Men | Women |
|---|---|---|
| FVC (liters) | 7.74 * Ht + 0.021 * A − 7.75 (0.51) | 4.14 * Ht − 0.023 * A − 2.20 (0.44) |
| $FEV_{1.0}$ (liters) | 5.66 * Ht − 0.023 * A − 4.91 (0.41) | 2.68 * Ht − 0.025 * A − 0.38 (0.33) |
| $FEV_{1.0}$/FVC (%) | 110.2 − 13.1 * Ht − 0.15 * A (5.58) | 124.4 − 21.4 * Ht − 0.15 * A (6.75) |
| $FEF_{25-75\%}$ (1/s) | 5.79 * Ht − 0.036 * A − 4.52 (1.08) | 3.00 * Ht − 0.031 * A − 0.41 (0.85) |

In a further embodiment, the functions of the server 136 are performed by the IMD 103, which directly generates the pulmonary performance assessment 153, for retrieval by an external device.

Normal, Obstructive and Restrictive Respiratory Patterns

Figure 5A:
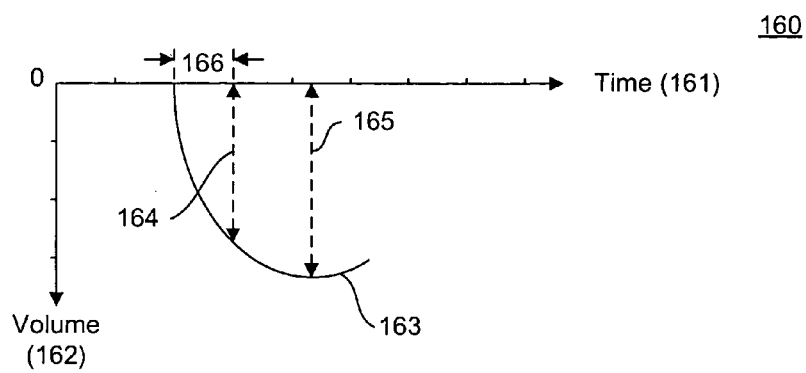
FIGS. 5A-C are graphical representations respectively showing, by way of example, normal, obstructive and restrictive respiratory patterns exhibited during forced expiration.
Figure 5B:
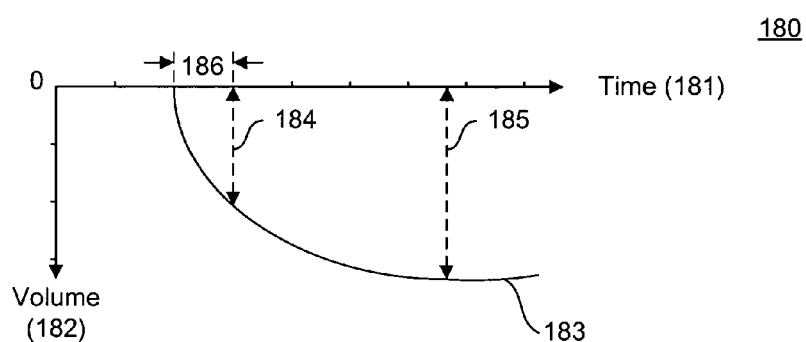
Figure 5C:
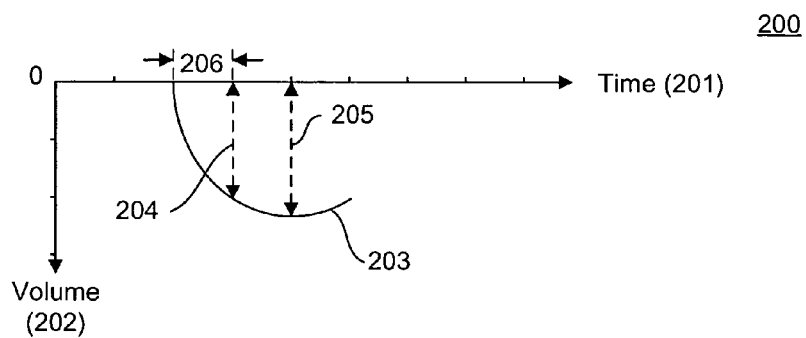

FIGS. 5A-C are graphical representations 160, 180, 200 respectively showing, by way of example, normal, obstructive and restrictive respiratory patterns exhibited during forced expiration. The x-axes 161, 181, 201 respectively represent time. The y-axes 162, 182, 202 respectively indicate volume. Pulmonary volume 163, 183, 203 is respectively plotted as a function of time. For clarity, the pulmonary volumes have been normalized relative to time and volume.

FEV is ordinarily measured over specified time periods, typically 0.5-, one-, two- and three-second periods. The one-second FEV measure ($FEV_{1.0}$) is representative of a patient's pulmonary performance capacity. The $FEV_{1.0}$ is applied over the observed FVC to generate a ratio indicative of ventilatory function performance. The ratio is compared as a percentage to predicted values.

Referring first to FIG. 5A, the pulmonary volume 163 for a healthy person is shown. $FEV_{1.0}$ 164 is measured at a one-second interval 166. The volume expired at the beginning of a forced exhalation is generally large and the ratio of $FEV_{1.0}$ 164 to FVC 165 is normally around 80 percent. In addition, the total amount of time required for completing the forced exhalation is typically less than three seconds.

Referring next to FIG. 5B, the pulmonary volume 183 for a patient with an obstructive respiratory pattern is shown. $FEV_{1.0}$ 184 is measured at a one-second interval 186. In contrast to the pulmonary volume profile of a healthy person, the rate of exhalation at the beginning of a forced exhalation is smaller due to increased airflow resistance caused by obstructions in the airway of the patient and the ratio of $FEV_{1.0}$ 184 and FVC 185 is normally around 42 percent.

Finally, referring to FIG. 5C, the pulmonary volume 203 for a patient suffering from a restrictive pulmonary disorder is shown. $FEV_{1.0}$ 204 is measured at a one-second interval 206. The volume expired at the beginning of a forced exhalation is similar to the pulmonary volume profile observed for a healthy person because the airway is open and unobstructed and the ratio of $FEV_{1.0}$ 204 over FVC 205 is normally around 90 percent. However, the total volume exhaled is significantly reduced due to restrictions on lung expansion and contraction, thereby resulting in a reduction in FVC 205 typically below 80 percent of normal healthy volume.

Trend Analysis for Volume Profile During a Forced Expiration

Figure 6A:
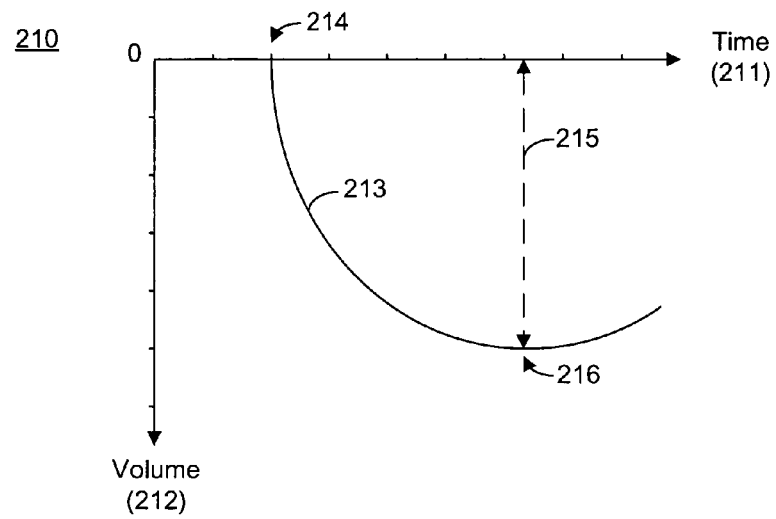
FIGS. 6A-B are graphical representations respectively showing, by way of example, volumetric and impedance values measured during an observation period using an implantable medical device.
Figure 6B:
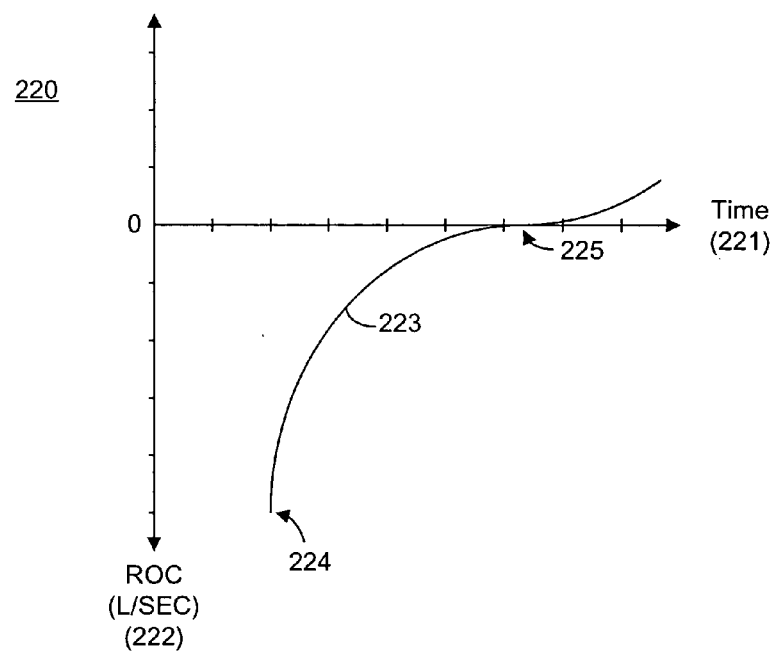

FIGS. 6A-B are graphical representations 210, 220 showing, by way of example, trend analysis for a volume profile during a forced expiration. The x-axes 211, 221 represent time. The y-axis 212 represents volume and the y-axis 222 represents rate of change of expired volume over time.

Referring first to FIG. 6A, pulmonary volume 213 is plotted as a function of time. Forced expiration starts at point 214 and ends at point 216, at which time the FVC 215 can be determined. Due to the rapid exhalation at the beginning, the rate of volume change as measured by the first order derivative of volume over time approaches infinity at the beginning of the expiration.

Referring next to FIG. 6B, the rate of change for the same forced exhalation described above with reference to FIG. 6A is measured beginning at point 224 and ending at point 225. The rate of change 223 can be used to perform a trend analysis of the forced pulmonary volume profile. During initial expiration, the pulmonary volume 213 is evaluated for a rapidly increasing trend, as indicated by a large rate of change 223. As the patient exhales further, the pulmonary volume 213 is evaluated for a slower increasing trend, as indicated by a smaller rate of change 223. When the patient has completed forced exhalation, the pulmonary volume 213 is evaluated for a zero rate of change, followed by an increasing rate of change 223. In particular, the maximum expiratory flow rate (MEFR) is the slope of a line connecting the points where 200 ml and 1200 ml has been exhaled, also referred to as forced expiratory flow ($FEV_{200-1200}$). The maximum midexpiratory flow rate (MMFR) is the slope of a line connecting the points where 25 percent and 75 percent of the FVC has been exhaled, also referred to as the $FEF_{25-75}$% percentile.

The trending profile information can be evaluated to provide evidence of impairment of ventilatory function. However, the trending profile information does not identify a specific disease process or disorder. Rather, abnormal pulmonary performance assessment results can indicate either an obstructive, restrictive or combination respiratory pattern. Three sets of pulmonary performance trends can be identified from the pulmonary volumetric and rate values obtained through transthoracic impedance measurements.

The first trend requires impedance sensor calibration and the establishment of a sensor baseline. The second set of trends only requires a sensor baseline. Finally, the third set of trends is immune to sensor calibration and sensor baseline establishment.

In evaluating the first pulmonary performance trend, FVC and FEV are measured during an initial observation period to establish a sensor baseline, following proper calibration of the impedance sensors using one or more electrodes 114a-b and 111a-b. Generally, the pulmonary volume profile trends indicating an obstructive pattern reflect increased airway resistance and decreased flow rates. In this pattern, the residual volume (RV) is increased and the RV to TLC ratio is markedly increased. In addition, flow rates, FEV to FVC ratios, MMFR, and MEFR are all decreased and the $FEV_{1.0}$ to FVC ratio is less than 75 percent. Additionally, the pulmonary volume profile trends indicating a restrictive pattern reflect decreased lung or thorax compliance or muscular weakness. The vital capacity and FVC are generally less than 80 percent of the predicted value, but the FEV to FVC ratios are normal. As well, TLC is decreased and RV/TLC ratio is normal.

Forced expiratory flow ($FEF_{25-75}\%$) can also be determined by identifying the middle half by volume of the total expiration and duration required. The $FEF_{25-75}\%$ is the volume in liters divided by the time in seconds. In patients with obstructive diseases, the $FEF_{25-75}\%$ is generally greater than their expected values. As well, comparing measured FVC, FEV and $FEF_{25-75}\%$ values by an implanted impedance sensor with predicted values from normal subjects can give diagnostic information of lung mechanics.

In evaluating the second pulmonary performance trend, a sensor baseline is established during an initial observation period and relative changes to FEV, FVC and component values are determined. A morphology indicative of restrictive respiratory patterns can be identified based on the relative changes to FEV, FVC and component values observed.

In evaluating the third pulmonary performance trend, the FEV to FVC ratios, $FEF_{25-75}\%$ and MMFR are determined without requiring sensor calibration and baseline establishment. A morphology indicative of chronic obstructive pulmonary diseases can be identified by values observed in the pulmonary performance trend.

Volumetric and Impedance Values

FIGS. 7A-B are graphical representations 230, 240 respectively showing, by way of example, volumetric and impedance values measured during an observation period using an implantable medical device. The x-axes 231, 241 represent time. Referring first to FIG. 7A, volumetric values 233 for respiration cycles are plotted as a function of time. The y-axis 232 represents relative volume. Referring next to FIG. 7B, impedance values 243 as measured through the sensors using one or more electrodes 114a-b and 111a-b on implantable medical device 103 are plotted as a function of time. The impedance 243 varies proportionately to the pulmonary volume 233 and can be used to directly measure actual pulmonary volume in a patient.

Pulmonary Performance Assessment Method

Figure 8:
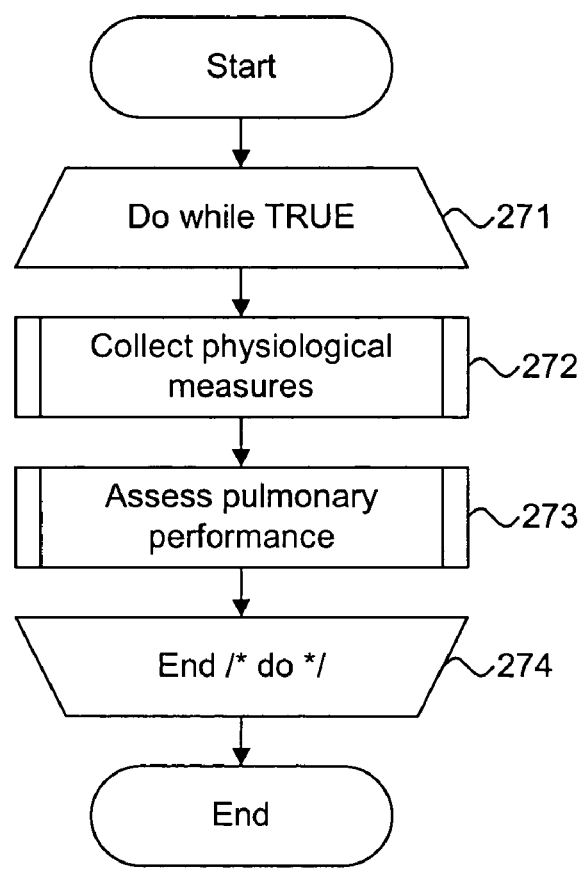
FIG. 8 is a flow chart showing a method for assessing pulmonary performance through transthoracic impedance monitoring, in accordance with a further embodiment of the present invention.

FIG. 8 is a flow chart showing a method 270 for assessing pulmonary performance through transthoracic impedance monitoring, in accordance with a further embodiment of the present invention. The method 270 is described as a sequence of process operations or steps, which can be executed, for instance, by a server 136 (shown in FIG. 3). In a further embodiment, the method 270 can be executed directly by the IMD 103 or related means, which generates a pulmonary performance assessment 153 for retrieval by an external device.

The method 270 preferably executes as a continuous processing loop (blocks 271-274). During each iteration (block 271), the physiological measures 145 are collected (block 272) from the IMD 103 and stored in the database 132, as further described below with reference to FIG. 9. Pulmonary performance is then assessed (block 273), as further described below with reference to FIG. 10. Processing continues (block 274), until the method exits or terminates.

Physiological Measures Collection

Figure 9:
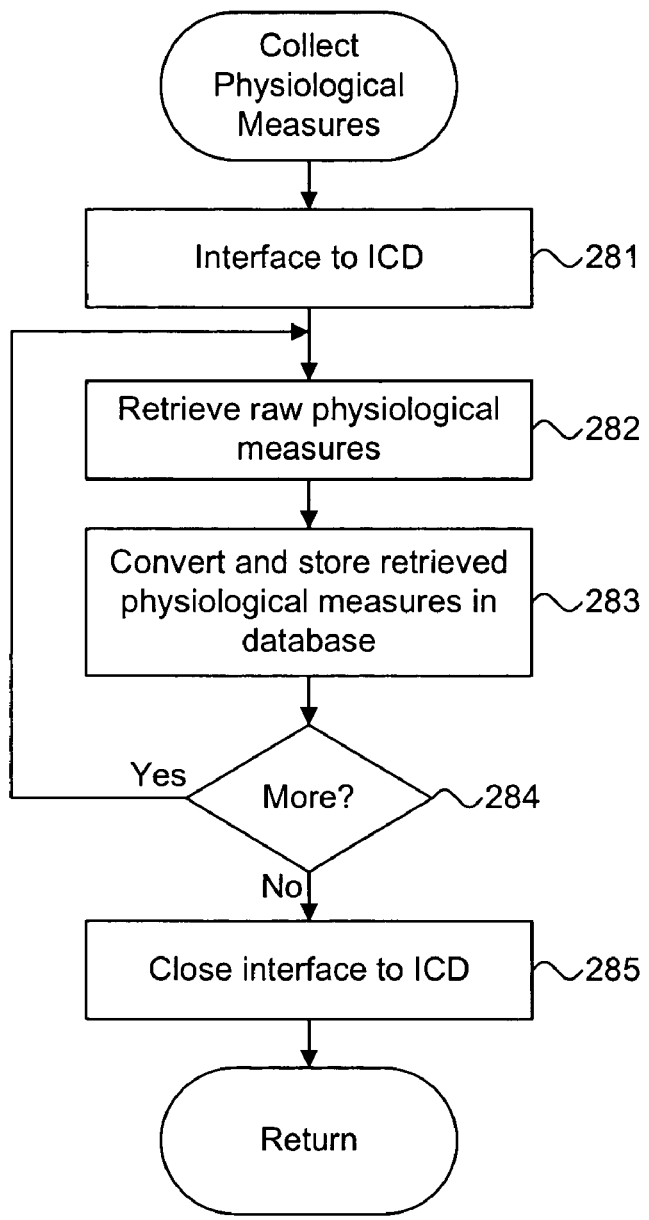
FIG. 9 is a flow chart showing a routine for collecting physiological measures for use in the method of FIG. 8.

FIG. 9 is a flow chart showing a routine 280 for collecting physiological measures 145 for use in the method 270 of FIG. 8. The purpose of this routine is to regularly interface to the IMD 103, retrieve the physiological measures 145 and store the retrieved physiological measures 145 in the database 132.

The routine begins initially by interfacing to the IMD 103 (block 281), using, for instance, inductive or static magnetic means, as would be appreciated by one skilled in the art. Raw physiological measures 145 are retrieved from the IMD 103 (block 282). The raw physiological measures 145 are converted and derived into impedance measures 147, pulmonary volumetric measures 148, pulmonary rate measures 149, and derived measures 150 and stored in the database 132 (block 283). If further physiological measures 145 require retrieval with the IMD 103 (block 284), processing continues. Otherwise, the interface to the IMD 103 is closed (block 285) and the routine returns.

Pulmonary Performance Assessment

Figure 10:
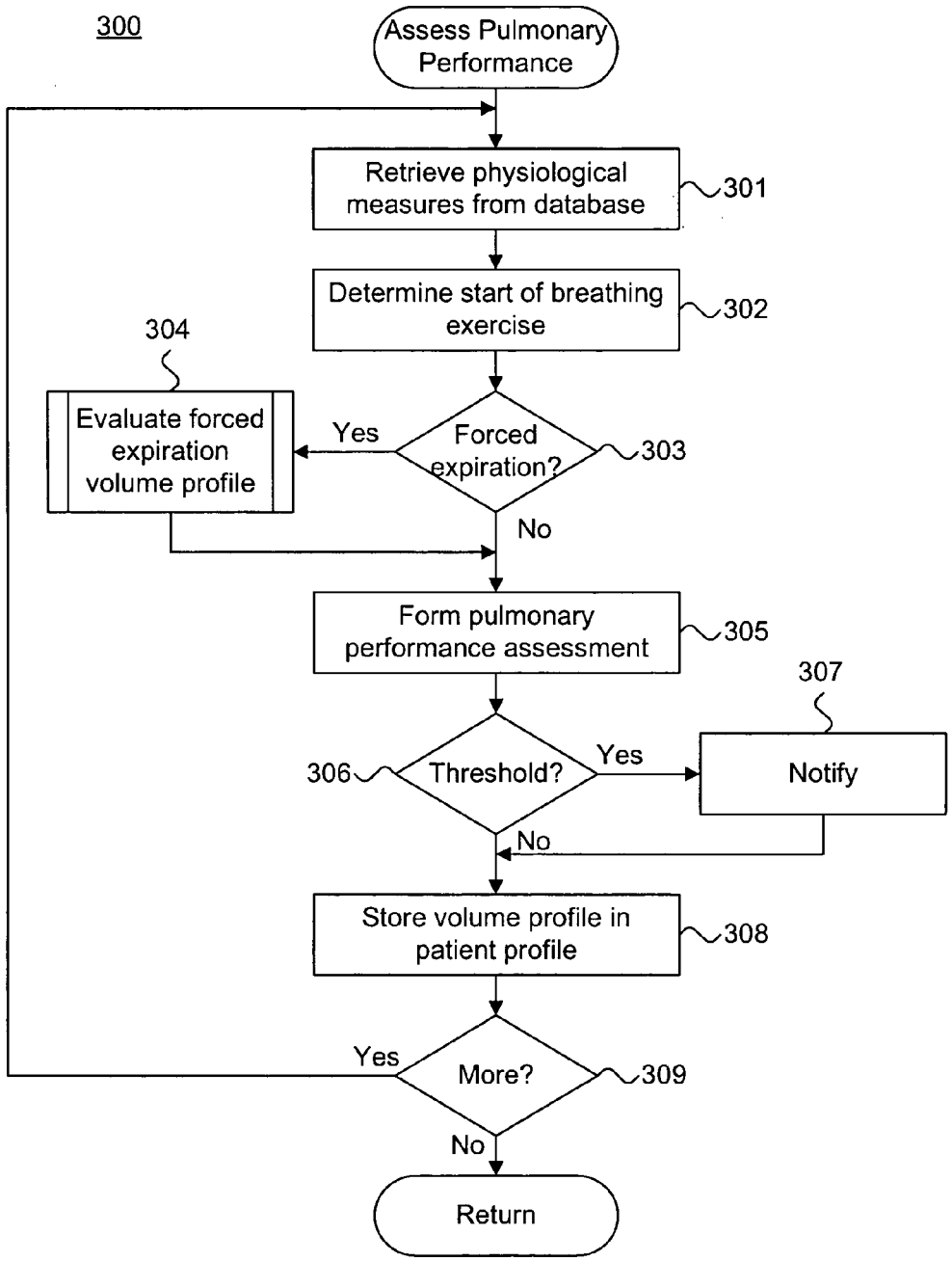
FIG. 10 is a flow chart showing a routine for assessing pulmonary performance for use in the method of FIG. 8.

FIG. 10 is a flow chart showing a routine 300 for assessing pulmonary performance for use in the method 270 of FIG. 8. The purpose of this routine is to periodically assess pulmonary performance through an analysis of the pulmonary volume profile trends identified by monitoring transthoracic impedance during the performance of at least one respiration cycle.

As an initial step, physiological measures, including impedance measures 147, pulmonary volumetric measures 148, pulmonary rate measures 149, and derived measures 150, are retrieved from the database 132 (shown in FIG. 3) (block 301). The start of the breathing maneuver, during which pulmonary performance is being assessed, is determined (block 302). The start of the maneuver is either expressly marked by the patient or implicitly derived by the IMD 103 or by a transthoracic pressure-sensing device. Typically, the breathing maneuver will be forced expiration (block 303). The forced expiration volume profile is then evaluated (block 304), as further described below with reference to FIG. 11.

Next, the pulmonary volume profile is evaluated to form a pulmonary performance assessment 153 (block 305). If the pulmonary performance assessment 153 substantially deviates from the predefined thresholds 152 (block 306), a notification is generated (block 307). In the described embodiment, predicted values, such as described above with reference to Table 1, are applied as the predefined thresholds 152. Notification takes the form of generating an alert for review and possible action by healthcare providers and can include generating appropriate feedback to the patient 100, such as described in commonly assigned U.S. Pat. No. 6,203,495, issued Mar. 20, 2001 to Bardy, disclosure of which is incorporated by reference.

If the pulmonary performance assessment 153 does not substantially deviate from the thresholds 152 (block 306), no notification is generated. The pulmonary volume profile is stored in a patient profile 151 (block 308) for use in further pulmonary performance trending analyses. If further retrieved physiological measures require evaluation (block 309), processing continues. Otherwise, the routine returns.

Evaluating Forced Expiration Volume Profile

Figure 11:
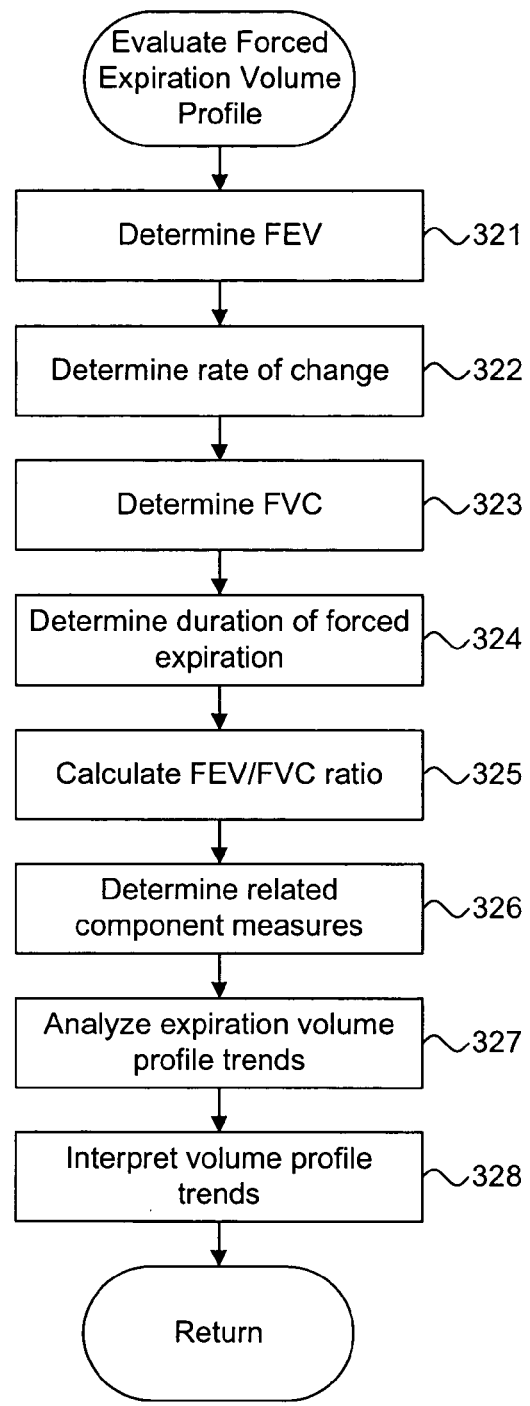
FIG. 11 is a flow chart showing a routine for evaluating a forced expiration volume profile for use in the routine of FIG. 10.

FIG. 11 is a flow chart showing a routine for evaluating a forced expiration volume profile 213 for use in the routine 300 of FIG. 10. The purpose of this routine is to evaluate a pulmonary performance assessment 153 by performing a trending analysis of observed pulmonary volume profiles correlated to forced expirations.

The FEV, rate of change and FVC are determined (blocks 321, 322 and 323 respectively). Similarly, the duration of the forced expiration is determined (block 324) and the FEV over FVC ratio is calculated (block 325). Related derived component measures, including MEFR, the $FEV_{1.0}$ to FVC ratio, TLC and the RV to TLC ratio, are determined (block 326). Finally, the expiration volume profile trends are analyzed (block 327) against the predicted values, as further described above with reference to Table 1. The volume profile trends are interpreted to identify evidence of impairment of ventilatory function (block 328), after which the routine returns.

While the invention has been particularly shown and described as referenced to the embodiments thereof, those skilled in the art will understand that the foregoing and other changes in form and detail may be made therein without departing from the spirit and scope of the invention.

What is claimed is:

1. A system for assessing pulmonary performance through transthoracic impedance monitoring, comprising:
   an implantable medical device to directly collect transthoracic impedance measures;
   a correlation component to correlate the transthoracic impedance measures to pulmonary functional measures relative to performance of at least one respiration cycle and to group the transthoracic impedance measures into at least one measures set corresponding to one of an inspiratory phase and an expiratory phase; and
   an analysis component to evaluate the pulmonary functional measures which were determined from the at least one transthoracic impedance measures set to identify a respiratory pattern relative to the inspiratory phase or the expiratory phase to represent pulmonary performance, comprising:
      a trending subcomponent to evaluate a trend in changes in the respiratory pattern relative to at least one previous respiratory pattern;
      a monitoring subcomponent to monitor the trend and the changes; and
      an alert subcomponent to compare the trends to thresholds and to generate an alert upon sufficient deviation from the thresholds.

2. A system according to claim 1, wherein the at least one respiration cycle comprises a forced expiration.

3. A system according to claim 2, wherein the pulmonary functional measures comprise at least one of volumetric, rate and derived measures.

4. A system according to claim 3, wherein the pulmonary functional measures further comprise at least one of respiration rate, tidal volume and minute ventilation.

5. A system according to claim 2, further comprising:
   a set of sensors to measure forced vital capacity and forced expiratory volume by respectively measuring a total volume exhaled during performance of the forced expiration and a volume expired during a tracked time period.

6. A system according to claim 5, wherein the forced vital capacity and the forced expiratory volume are analyzed to characterize one of an obstructive respiratory pattern and a restrictive respiratory pattern.

7. A system according to claim 2, further comprising:
   a set of sensors to measure a forced expiratory flow by identifying a middle volume of the forced expiration and tracking a duration of the forced expiration.

8. A system according to claim 2, further comprising:
   a derivation subcomponent to derive at least one of a ratio of forced expiratory volume to forced vital capacity and a maximal midexpiratory flow rate.

9. A system according to claim 8, further comprising:
   a comparison subcomponent to respectively compare the at least one of the forced expiratory volume to forced vital capacity ratio and the maximal midexpiratory flow rate to predicted values of the forced expiratory volume to forced vital capacity ratio and the maximal midexpiratory flow rate.

10. A system according to claim 2, wherein the implantable medical device is calibrated and a baseline set of transthoracic impedance measures is established.

11. A system according to claim 2, further comprising:
    a reference electrode and a sensor to measure blood pH through the implantable medical device; and
    control circuitry to determine pH information from the measured blood pH.

12. A system according to claim 2, wherein the implantable medical device comprises at least one of an implantable cardiac pacemaker, an implantable cardioverter defibrillator, an implantable cardiac resynchronization device, an implantable cardiovascular monitor, and a therapeutic device that monitors and treats structural problems of the heart.

13. A system according to claim 2, further comprising:
    a communication subcomponent to communicate the pulmonary performance through at least one of an implantable medical device and a non-implantable medical device.

14. A system according to claim 2, further comprising:
    a sensor to measure oxygen saturation through the implantable medical device; and
    control circuitry to determine blood gases from the measured oxygen saturation.

15. A method for assessing pulmonary performance through transthoracic impedance monitoring, comprising:
    directly collecting transthoracic impedance measures through an implantable medical device;
    correlating the transthoracic impedance measures to pulmonary functional measures relative to performance of at least one respiration cycle;
    grouping the transthoracic impedance measures into at least one measures set corresponding to one of an inspiratory phase and an expiratory phase; and
    evaluating the pulmonary functional measures which were determined from the at least one transthoracic impedance measures set to identify a respiratory pattern relative to the inspiratory phase or the expiratory phase to represent pulmonary performance, comprising:
       evaluating a trend in changes in the respiratory pattern relative to at least one previous respiratory pattern;

monitoring the trend and the changes;
comparing the trends to thresholds; and
generating an alert upon sufficient deviation from the thresholds.

16. A method according to claim 15, wherein the at least one respiration cycle comprises a forced expiration.

17. A method according to claim 16, further comprising:
measuring oxygen saturation through the implantable medical device; and
determining blood gases from the measured oxygen saturation.

18. A method according to claim 16, further comprising:
measuring arterial pH through the implantable medical device; and
determining pH information from the measured arterial pH.

19. A method according to claim 16, wherein the pulmonary functional measures comprise at least one of volumetric, rate and derived measures.

20. A method according to claim 19, wherein the pulmonary functional measures further comprise at least one of respiration rate, tidal volume and minute ventilation.

21. A method according to claim 16, further comprising performing at least one of an implantable cardiac pacemaker therapy, an implantable cardioverter defibrillator therapy, an implantable cardiac resynchronization therapy, an implantable cardiovascular monitoring, and a therapeutic device that monitors and treats structural problems of the heart.

22. A method according to claim 16, further comprising:
measuring forced vital capacity and forced expiratory volume by respectively measuring a total volume exhaled during performance of the forced expiration and a volume expired during a tracked time period.

23. A method according to claim 22, further comprising:
analyzing the forced vital capacity and the forced expiratory volume characterizing one of an obstructive respiratory pattern and a restrictive respiratory pattern.

24. A method according to claim 16, further comprising:
measuring a forced expiratory flow by identifying a middle volume of the forced expiration and tracking a duration of the forced expiration.

25. A method according to claim 16, further comprising:
deriving at least one of a ratio of forced expiratory volume to forced vital capacity and a maximal midexpiratory flow rate.

26. A method according to claim 25, further comprising:
respectively comparing the at least one of the forced expiratory volume to forced vital capacity ratio and the maximal midexpiratory flow rate to predicted values of the forced expiratory volume to forced vital capacity ratio and the maximal midexpiratory flow rate.

27. A method according to claim 16, further comprising:
calibrating the implantable medical device; and
establishing a baseline set of transthoracic impedance measures.

28. A method according to claim 16, further comprising:
communicating the pulmonary performance through at least one of an implantable medical device and a non-implantable medical device.

29. An apparatus for assessing pulmonary performance through transthoracic impedance monitoring, comprising:
means for directly collecting transthoracic impedance measures through an implantable medical device;
means for correlating the transthoracic impedance measures to pulmonary functional measures relative to performance of at least one respiration cycle;
means for grouping the transthoracic impedance measures into at least one measures set corresponding to one of an inspiratory phase and an expiratory phase; and
means for evaluating the pulmonary functional measures which were determined from the at least one transthoracic impedance measures set to identify a respiratory pattern relative to the inspiratory phase or the expiratory phase to represent pulmonary performance, comprising:
means for evaluating a trend in changes in the respiratory pattern relative to at least one previous respiratory pattern;
means for monitoring the trend and the changes;
means for comparing the trends to thresholds; and
means for generating an alert upon sufficient deviation from the thresholds.

* * * * *